US012343412B2

(12) United States Patent
D'Alessandri

(10) Patent No.: US 12,343,412 B2
(45) Date of Patent: Jul. 1, 2025

(54) DYNAMIC MAKE-UP PRODUCT

(71) Applicant: VENTISEIDIECI S.R.L., Rome (IT)

(72) Inventor: Riccardo D'Alessandri, Rome (IT)

(73) Assignee: Hydraink S. R. L., L'Aquila (IT)

( * ) Notice: Subject to any disclaimer, the term of this patent is extended or adjusted under 35 U.S.C. 154(b) by 1176 days.

(21) Appl. No.: 17/256,989

(22) PCT Filed: Jul. 23, 2019

(86) PCT No.: PCT/IB2019/056267
§ 371 (c)(1),
(2) Date: Dec. 29, 2020

(87) PCT Pub. No.: WO2020/021443
PCT Pub. Date: Jan. 30, 2020

(65) Prior Publication Data
US 2021/0127813 A1     May 6, 2021

(30) Foreign Application Priority Data

Jul. 25, 2018  (EP) ..................................... 18185612

(51) Int. Cl.
| | | |
|---|---|---|
| *A61K 8/19* | (2006.01) | |
| *A45D 34/00* | (2006.01) | |
| *A45D 34/04* | (2006.01) | |
| *A61K 8/02* | (2006.01) | |
| *A61K 8/06* | (2006.01) | |
| *A61K 8/92* | (2006.01) | |
| *A61Q 1/02* | (2006.01) | |
| *A61Q 1/04* | (2006.01) | |

(Continued)

(52) U.S. Cl.
CPC .............. *A61K 8/19* (2013.01); *A45D 34/043* (2013.01); *A45D 34/045* (2013.01); *A61K 8/02* (2013.01); *A61K 8/0204* (2013.01); *A61K 8/025* (2013.01); *A61K 8/06* (2013.01); *A61K 8/92* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61Q 3/02* (2013.01); *A45D 2034/005* (2013.01); *A61K 2800/412* (2013.01); *A61K 2800/413* (2013.01); *A61K 2800/42* (2013.01); *A61K 2800/47* (2013.01); *A61K 2800/651* (2013.01); *A61K 2800/87* (2013.01); *A61K 2800/872* (2013.01); *A61K 2800/88* (2013.01)

(58) Field of Classification Search
None
See application file for complete search history.

(56) References Cited

PUBLICATIONS

Ge et al ("Magnetochromatic Microspheres: Rotating Photonic Crystals", Journal of American Chemical Society, vol. 131 (43) (2009), p. 15687-15694) (Year: 2009).*

* cited by examiner

*Primary Examiner* — Sin J Lee
(74) *Attorney, Agent, or Firm* — R. Ruschena Patent Agent, LLC

(57) ABSTRACT

Dynamic make-up product having in its formulation magneto-chromatic microspheres, which modify their orientation and therefore the color of the make-up product under the action of a magnetic field, wherein said dynamic make-up product, once exhausted, is configured to be recharged by means of a refill containing interchangeable capsules inside which the dynamic make-up product is contained. The refill is inserted in a casing having all the magnetic side surfaces which cooperate with a magnetic field source generating a magnetic force.

2 Claims, 5 Drawing Sheets

(51) Int. Cl.
*A61Q 1/06* (2006.01)
*A61Q 1/08* (2006.01)
*A61Q 1/10* (2006.01)
*A61Q 1/12* (2006.01)
*A61Q 3/02* (2006.01)

DYNAMIC MAKE-UP PRODUCT

CROSS REFERENCE TO RELATED APPLICATIONS

This is a national stage application of PCT application PCT/M2019/056267 having an international filing Date of Jul. 23, 2019. This application claims foreign priority based on application 18185612.1 filed with the European Patent Office on Jul. 25, 2018.

FIELD OF THE INVENTION

The present invention relates to an innovative make-up product in the make up sector and a method for implementing said product. In particular, this make-up product is based on a new technology that includes the creation of make-up products based on magneto-chromatic microspheres, able of transforming the surface of the body, on which the product is applied, into an interactive platform.

The invention therefore relates to make-up products incorporating materials that change color in response to an externally applied magnetic force, by an electronic device (controlled by computer applications) and by a method for implementing the product itself.

BACKGROUND OF THE INVENTION

As is known, make-up has ancient origins, all the make-up products that we have available today is the result of centuries of history, discoveries and traditions that have evolved over time and intersected gradually with science and especially with medicine. The cult of beauty or the personal care was already widespread in ancient Egypt: Cleopatra's people were among the first to develop a wide range of make-up products and to document their importance in their culture. The Egyptians used Kohl, a dark colored powder obtained by grinding the burnt of almonds, lead and copper, minerals, ash and ocher all processed substances that were applied to the eyes with a stick to give the eye an almond look, considered very attractive. But, not only make-up: the heavy make-up of the ancient Egyptians, especially the beautiful queens like the legendary Nefertiti, not only served to make their eyes colorful, seductive and brilliant, but had a real preventive and therapeutic function, with the make-up actually shielded the eyes from infections.

Already from the first century, even the Romans used the Khol for the makeup of eyelashes and eyebrows. Roman women in the late third century B.C. they began to wear long hair in very elaborate hairstyles, made up of overlapping curls. The dyes were very used, and the favorite color was blond-red. Her lips were dyed red using ocher powder, and her face and arms were whitened with white or chalk, the eye contour was blackened with soot. To whiten and soften the skin, donkey milk was used and to give it freshness, instead, they sprinkled it with cerussa, a cream based on the poisonous lead oxide. Around the Victorian period, facial makeup began to be associated with actresses. Women resorted to extreme measures to appear with a diaphanous skin using ingredients like lead and arsenic. Not even the sun was well seen: the skin to be young and healthy had to be protected by veils and umbrellas. Natural ingredients such as oatmeal, honey, egg yolks, and roses replaced make-up products. The eyebrows were redesigned and powdered rice was used on the face and decollete.

In 1930 the trick was used by women of all social classes. The mouth was colored in the shape of a heart within the natural contours that were covered with foundation. The eyebrows were thin and sagging, as well as the shape of the eyes, helping to determine that typically languid appearance.

The make-up in the 70s becomes even more exasperated. The accent remains on the eyes, the false eyelashes appear. The lips are colored with pearlescent and pale hues. The ingredients used for these first make-up products of the modern era are vegetables: glycerin, seed oil, lanolin, beeswax, but in a short time, the growing oil industry provides low-cost mineral derivatives: vaseline oil, vaseline streamer, paraffin. In the 80s the trend-setting make-up was heavy, accentuated, dark and dramatic eyes, made up with the help of many layers of eyeliner and bright eyeshadows in blue, green and purple shades. A metallic powder produced with a mineral, mica, becomes famous for use on the eyelids and on the body to obtain brilliant reflections.

Anthropology teaches us that make-up, since its beginnings, arises not only with the function of embellishing the body image, but that has to do with the concept of identity and cultural belonging to different ethnic groups and races. Just to name a few examples, think of Native Americans and their typical costumes and colors that sanction their belonging to a certain tribe, Indian women who usually wear their foreheads to communicate their new status to the world, to the indigenous peoples tribes that make up even more during the holidays. In all these cases make-up is a form of strong communication that has the meaning of differentiating itself from others.

Today this meaning has remained partly intact, although transposed in our way of living the world. From this point of view, therefore, the trick, for the African tribes as for today's and tomorrow's teenagers, has a very similar communicative function.

There exist at the state of the art several make-up compositions belonging to the make-up family, made in different chemical forms. In fact make-up different families of products: the powders (which are divided into free, compact, cooked and extruded), the anhydrous (which are subdivided into castings and extruded), emulsions (which are divided into oil in water, water in oil, water and silicone, water and silicone), pencils (in wood or plastic), enamels and various (oils, gels, ointments, pastes and solutions).

The powders can be free, compact, cooked (water is removed) and extruded (similar to chalks). The make-up products in the form of powder that we can find on the market are: powders, compact foundations, earths, blushes, eye shadows and powders for the body. The areas of application of the powders are: face (powders, foundation, blush, earth), eyelids (eye shadows) and body (talcum powder and aspersor powder). The powders must meet certain technical requirements: covering power, opaque appearance, adhesiveness, absorbency, smoothness. Among the powders, one of the most widespread products is certainly face powder. Face powder is a mixture of porous multi-powders, generally of mineralized origin, combined with silicone and synthetic oils that characterize the laying and adherence to the epidermis. Face powder in turn is divided into compact and loose powder. The compact face powder is the most common and is colored. It has a composition with a high quantity of binding substances and pigments. Face powder is used as an alternative to foundation and especially for make-up touch-ups during the day. The loose face powder is transparent or only slightly colored and is used to fix the makeup, without weighing it down and altering the color of the foundation previously applied.

The anhydrous compounds are chemical compounds without water and are distinguished in castings and extrusions. Lipsticks, glosses, concealers, eye shadows, blushes, foundations, eyeliner and mascaras are anhydrous. The solutions are homogeneous mixtures formed by a dispersed component (solute) in a dispersing medium (solvent). In the make-up field, the solutions used can be hydroalcoholic or aqueous and contain salts, extracts and other water-soluble substances. When a substance is dispersed in a liquid forming a transparent and clear solution, it means it is a soluble substance. When two liquids are soluble in each other they are said to be miscible. Examples of make-up products in solutions are tonics, lotions, balsams, detergents and clutches. The emulsion is the very fine dispersion of one liquid in another with which it cannot be mixed. The mixing of the two phases is made possible by emulsifying agents. The main types of emulsions are:

Oil in water (O/W): the oil is dispersed in water and the aqueous part has a higher percentage. They are emulsions used for sunscreen products and for creams dedicated to dry or oily skin.

Water in oil (W/O): the water is dispersed in the oil and the oily part has a higher percentage. This type of emulsions are slightly oily.

In general emulsions are more or less fluid creams (such as foundation and primer), mascara, eyeliner, lipstick and some hair products.

The pencil in makeup is a make-up product available on the market in different types: for the lips, for the eyes, for the eyebrows. Each different part of the face to be treated requires a different type of pencil. The difference between one pencil and another depends on the mine: soft pencils are recommended for the eyes, while hard pencils are used for the lips and eyebrows.

Nail polish is a make-up product for coloring and protecting nails. Nail polish contains a mixture of inorganic pigments and other functional ingredients. The more concentrated these substances are, the more the enamel will take on a more or less charged tone.

It is known that structural coloring is the production of color with microscopically structured surfaces that are thin enough to interfere with visible light, sometimes in combination with pigments. For example, the peacock tail feathers are brown pigmented, but their microscopic structure also makes them reflect blue, turquoise and green light, and are often iridescent.

Structural staining was first observed by British scientists Robert Hooke and Isaac Newton and its principle—wave interference—explained by Thomas Young a century later. Young described iridescence as the result of interference between the reflections of two or more thin film surfaces, combined with the refraction when light enters and leaves such films. The geometry then determines that in certain angles, the light reflected from both surfaces interferes constructively, while in other angles, the light interferes destructively. The different colors then appear at different angles.

In animals such as bird feathers and butterfly scales, interference is created by a series of photonic mechanisms, including diffraction gratings, selective mirrors, photonic crystals, crystalline fibers, nanochannel matrices and proteins that can vary their configuration.

It is also known that subjecting a liquid suspension of clusters of colloidal nanocrystals of iron oxide to a magnetic field causes the assembly of the colloidal nanocrystals clusters (CNC, i.e., magneto-chromatic microspheres) into periodic matrices which form a photonic crystal which diffuses the light in the visible spectrum, as well as in ultraviolet and infrared spectra. Adjusting the magnetic field strength applied to the CNC alters the photonic crystal structure and thus the wavelength (color) of the diffracted light. In other words, the color displayed by the CNC can be controlled by modifying the strength of a magnetic field applied to a suspension containing the CNCs.

One of the first publications describing the development of particles that have the attributes of color change, i.e. the development of superparamagnetic magnetite ($Fe_3O_4$) CNC, is document N. WO2009/017525. Polyacrylic acid is used as surfactant for the strong coordination of carboxylated groups with iron cations on the magnetite surface. A further document is N. WO2009/017525 which also describes a method for the production of colloidal photonic crystals from the superattramagnetic magnetothermal CNCs coated with polyacrylate. These CNCs easily assemble in colloidal photonic crystals in polar solvents (for example water and alkanols) making it possible to apply a magnetic field. The optical responses of the photonic crystals are rapid and completely reversible. Also document N. WO2010/096203 teaches a method of assembling superparamagnetic CNCs in colloidal photonic crystals in non-polar solvents creating long-range electrostatic repulsive forces on the CNCs using charge control agents. The method comprises coating the CNCs with a hydrophobic coating so that the CNCs are soluble in a non-polar solvent solution and adding a surfactant (charge control agent) to the non-polar solvent solution, wherein the surfactant increases charge separation between the CNCs to form an ordered structure with separation of the tunable particles. Finally, the document N. WO2012/122216 describes a method for the manufacture of fixed individual nanochenes with magnetic photonic properties, in which the CNCs are coated with a silica layer; a magnetic field is applied to the CNCs to assemble the CNCs in photonic chains and the photonic chains are then coated with a further layer of silica. The particle chains are then permanently fixed by the silica overlap so that they are retained when dispersed in solution or dried on solid substrates.

While the composition of materials and processes for creating make-up products have evolved, the latter remain static. In fact, there are no known applications of magneto-chromatic microspheres in make-up products such as to make the make-up dynamic and interactive. However, because current social contexts require different representations of ourselves, it is often necessary several times during the day, and depending on the context, to completely change the make-up. This practice obviously requires a lot of time and the availability of numerous make-up products with different colors.

There is therefore the need to define an innovative dynamic make-up product, able to change color instantly, after being applied only once and a method to implement the "dynamism" of the same make-up product. In this way the user has the ability to automatically change the color of his make-up according to different social scenarios without the need to remove and put back make-up. Microspheres of microscopic polymers that change color instantly and reversibly when the external magnetic fields acting on the microspheres change orientation, were fabricated by a research group at the University of California, in Riverside (UCR). The beads or "magneto-chromatic microspheres" have an excellent structural stability. They are also highly compatible with various types of dispersion media such as water, alcohol, hexane and even polymer solutions, allowing them to store magnetically tunable colors in a variety of chemical environments. Contrary to traditional methods, the instant and reversible color change in the polymer microspheres takes place without any change in their structural and intrinsic properties. The mechanism involves the dispersion of these magneto-chromatic microspheres in a liquid such as water, alcohol and hexane or polymer solution. These microspheres contain iron oxide nanostructures that rotate due to the external magnetic field acting on it, thus making an instant color change in the polymer spheres. The color observed in the new materials is "structural color" because it is caused by interference effects rather than pigments. Conventional methods of producing tunable color changes depend on difficult to reach and slow process techniques such as changing the periodicity of the array or the refractive index of the materials. In this new method, the color is tuned by changing the relative orientation of the periodic arrays in the microspheres using the external fields appropriately. When the material is subjected to a magnetic field, the distances between the nanoparticles are adjusted, thus allowing visualization of any color in the visible spectrum (FIG. 1).

SUMMARY OF THE INVENTION

An object of the present invention is therefore an innovative make-up product, i.e. a make-up article such as lipstick, gloss, eye shadow, etc., comprising reversible color magneto-chromatic microspheres by applying an external magnetic field, and a method for variation of the color of the same product, or for the implementation of the "dynamism" of the make-up. Such microspheres are, for example, colloidal iron oxide nanocrystals arranged inside chains, incorporated in the make-up product formulation; such nanocrystals allow to visualize a color determined by an external force applied to the make-up product. This make-up product comprises magneto-chromatic microspheres capable of being mutated by an external device to vary the color of the makeup without having to resort to the reapplication thereof, as specified in the independent claim of the annexed product.

The method for color variation of the dynamic make-up product is specified in the annexed independent method claim, while the system for implementing the method is specified in the independent apparatus claim.

The dependent claims outline particular and further advantageous aspects of the invention.

BRIEF DESCRIPTION OF THE DRAWINGS

These and other advantages of the invention will now be described in detail, with reference to the accompanying drawings, which represent an exemplary embodiment of the invention, in which.

DETAILED DESCRIPTION OF VARIOUS EMBODIMENTS

With reference to the attached figures, a dynamic make-up product 1 is shown, in particular a lipstick for the lips, the color of which is modified through the application of a magnetic field generated by a wearable electronic device 3. The polarity of the magnetic force produced electronic wearable device is controlled by a computer application 2, for example an application for a Smartphone or Smartwatch.

In particular, the wearable electronic device 3 has within it a wireless communication system and a magnetic emitter activated through electromagnetism or mechanical movement. The dynamic make-up product 1 has inside colored magneto-chromatic microspheres 10 which according to the magnetic field applied to them will rotate aligning and showing the desired color.

The dynamic make-up product 1, for example a lipstick, includes in its formulation, in addition to the magneto-chromatic microspheres 10, the following components:

a base made up of waxes (to give stability, resistance and film-forming action), oils of various origins (to guarantee brightness, softness and dispersion of the pigments);

dye with natural pigments (iron oxides) or synthetic (lacquers) which give the color to the lipstick;

preservatives;

antioxidants to prevent rancidity of the oily component and perfumes;

texturizing to guarantee the sensory effect;

functional substances: moisturizing, anti-aging, increasing volume, emollient;

emulsifiers (for an aqueous base that must be combined with the oily one) The magneto-chromatic microspheres may be in the form of powder with different granulometries or in solutions stabilized in non-polar solvents. The application of the magnetic field and the relative color change takes place thanks to the charge of a surfactant (emulsifying agent) added to the non-polar solution in which the magneto-chromatic microspheres are inserted. The non-polar environment which stabilizes the magneto-chromatic microspheres is also guaranteed by the oil phase (phase A).

Example of Formulation

Figure 5:
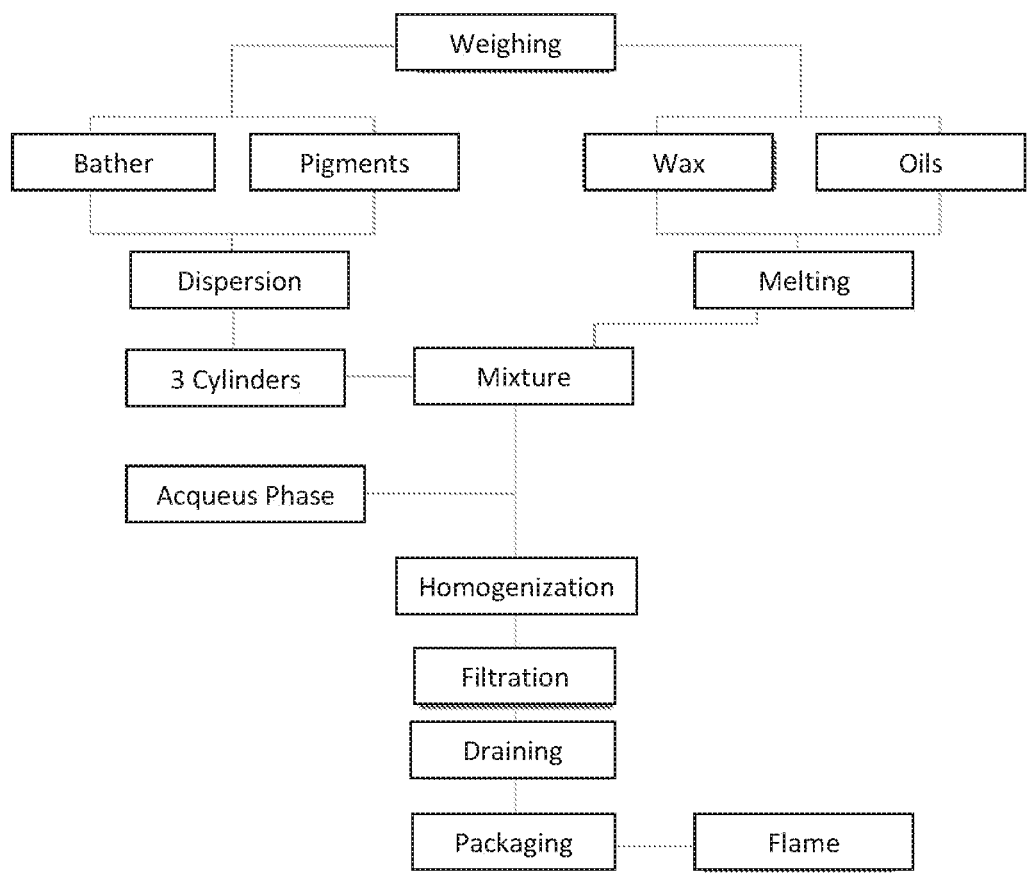
FIG. 5 shows a block diagram relating to the production of a dynamic make-up, according to an embodiment of the present invention.

As shown in the block diagram of FIG. 5, the dynamic make-up product 1, for example a lipstick is made as described below. The waxes are melted together with the oils and brought to 75° C.; the rheological modifiers are dissolved or dispersed in the molten mass, then adding the emulsifier and texturizers (phase A). The pigments and the magneto-chromatic microspheres are dispersed in a fraction of the collected mass (phase B). The dispersion is immediately refined in the three cylinders machine and then joined again in the fat phase. Separately, the ingredients of the aqueous phase are weighed and brought to 75° C. At this point the aqueous phase is slowly added to the fat phase under vigorous stirring or by homogenizer. The obtained emulsion is poured into the appropriate molds and left to cool at room temperature.

Then method for the color variation of a dynamic make-up product 1 containing magneto-chromatic microspheres 10 is carried out by means of a magnetic field source, preferably wearable, in which the force of the generated magnetic field is manageable through external computer systems or a computer application to manage the polarity and intensity of the magnetic field source.

The magnetic field source can be an electronic device 3 or the casing 12 of the dynamic make-up product 1.

The method is implemented through the following steps:
apply the dynamic make-up product according to the normal methods of application of makeup,
activate a field source generating the strength of the magnetic field manageable through external IT systems
activate a computer application to manage the polarity and intensity of the magnetic field source.

Figure 1:
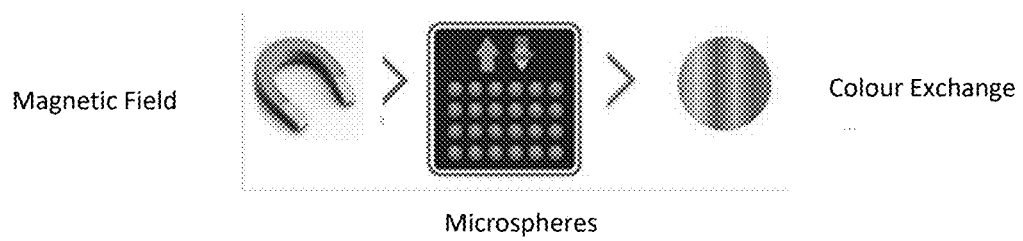
FIG. 1 shows the effect of external magnetic fields on the microspheres, which produces a change in orientation of the microspheres and consequently a color change, allowing the display of any color in the visible spectrum, according to the prior art.
Figure 2:
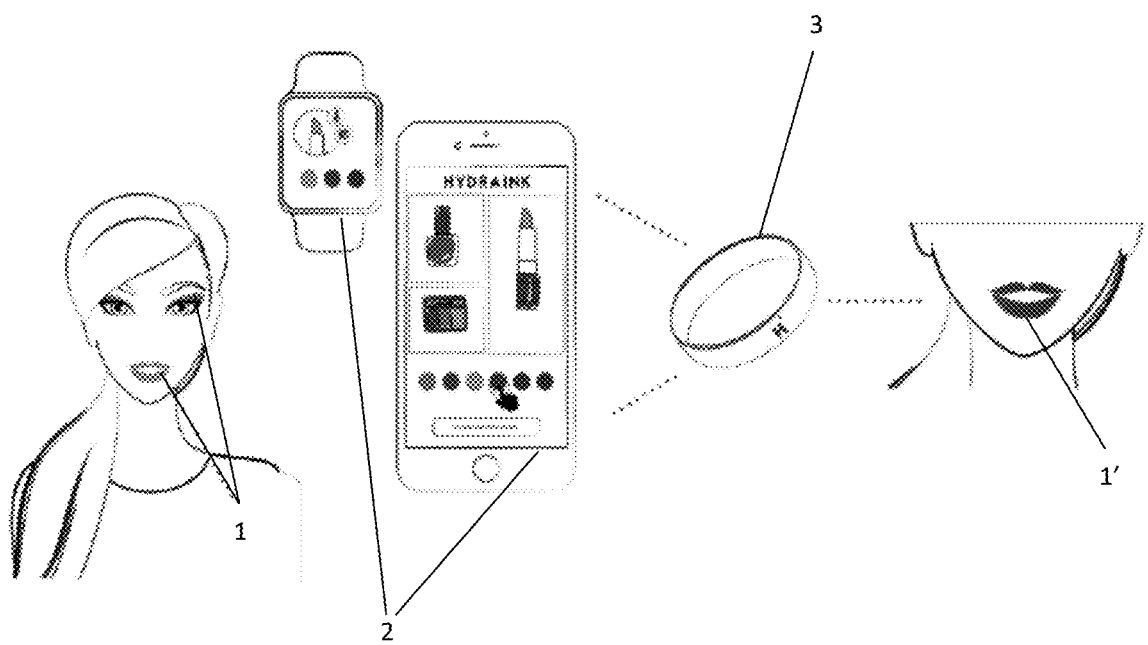
FIG. 2 shows a simplified diagram of the system according to the present invention.

As shown in FIG. 2 after applying the dynamic make-up product 1, for example a pink lipstick on the lips, this color can be modified, without having to resort to the reapplication thereof, simply by using a computer application 2 capable of interacting with a device electronic wearable 3 provided with a magnetic source which, interfering with the magneto-chromatic microspheres present in the applied dynamic make-up product 1 allows the variation of its color, in the case, for example, a red lipstick 1'.

Figure 3:
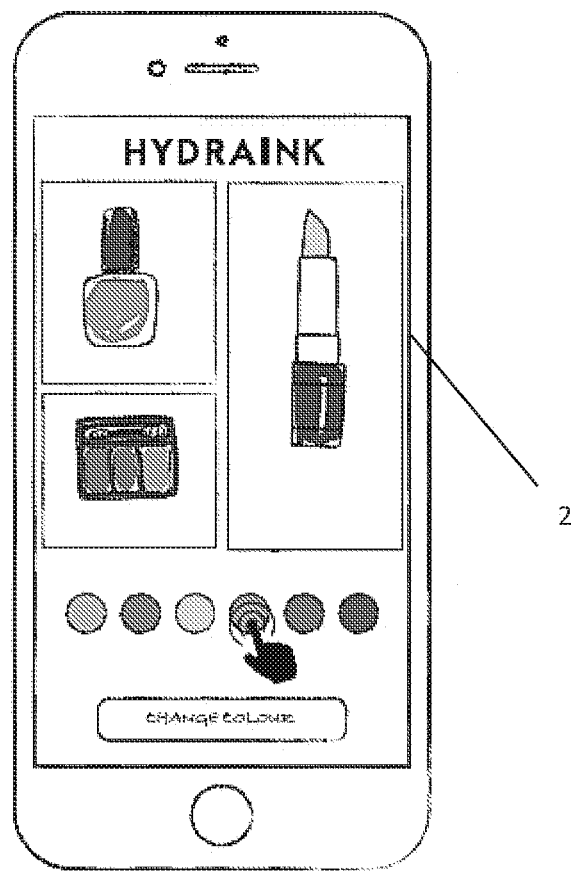
FIG. 3 shows the computer interface in the form of a mobile application for Smartphone through which the color of the make-up is made.
Figure 4:
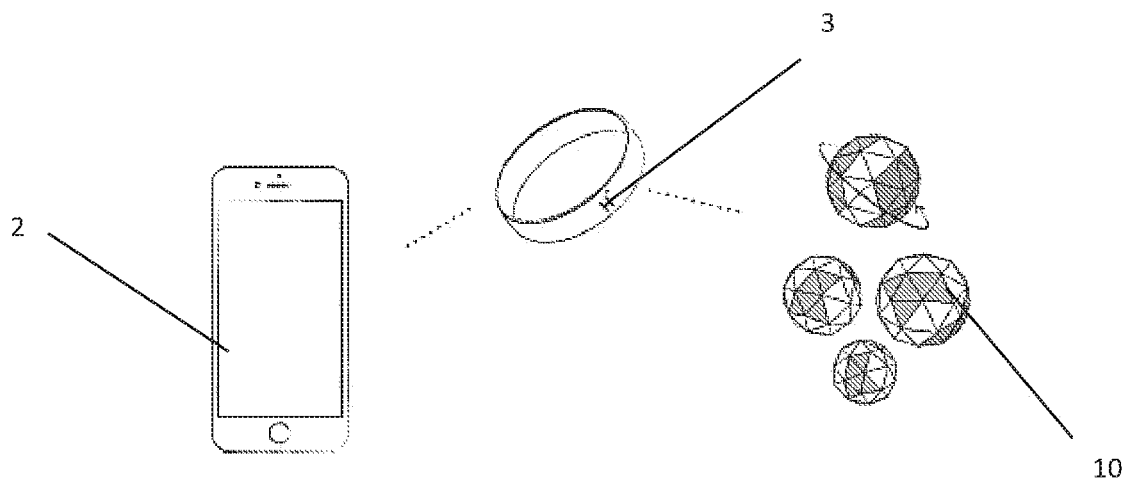
FIG. 4 shows the interaction between the computer interface of FIG. 2 and the magneto-chromatic microspheres of the dynamic make-up product.
Figure 8:
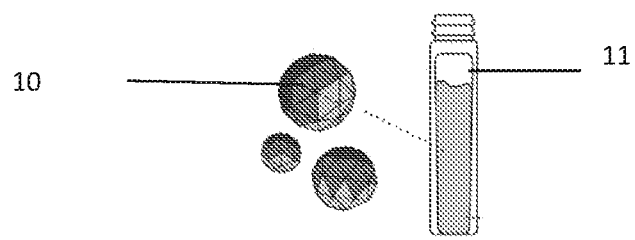
FIG. 8 shows a charging capsule.

By activating a computer application 2 present on a smartphone (see FIG. 3) or a smartwatch you can select the applied dynamic make-up product 1 and view the possible color variations of the dynamic make-up product 1. This simulates the selection of the color of the lipstick for example red, as shown in FIG. 2. The computer application will then communicate wirelessly with the wearable electronic device 3 (for example a ring, a bracelet, etc.) or directly with the casing 12 of the product, for example the one shown in FIG. 6, the intensity and the magnetic polarity to be applied to the make-up product 1 according to the color selection made on the application by the user. Approaching the wearable electronic device 3 to the make-up product 1, the magneto-chromatic microspheres 10 (as shown in FIG. 4 and FIG. 8) will orient themselves showing the desired color. At this point the color of the dynamic make-up product 1 will be changed with respect to that applied at the origin. The color will remain stable until the next color change desired, which can be done by going over the steps described and anyway whenever the user wants it, until the removal of the make-up itself.

Advantageously, the dynamic make-up product, once exhausted can be recharged. The refill is achieved through the use of capsules for product refills without having to change the casing of the dynamic make-up product. In particular, the different make-up products contained within the capsules with the chosen dynamic color or make-up product can be inserted inside the casing to be refilled to be used again for applying makeup. In this way, using the refills directly inserted into the casing, the problem of the formation of bacteria inside make-up products is also eliminated. In fact, by charging with the capsules, the product never comes into contact with the outside. Each capsule is sealed and is vacuum-sealed, maintaining in this way the quality and purity of the product unaltered. The deadline is indicated digitally, through a notification on the mobile device of use. Advantageously, even in this case, the color of the refill is selected and this changes the shades to create the customized color every time you want to change your make-up. Capsule refills are available in over a hundred different colors to create specific shades or color changes.

Figure 7:
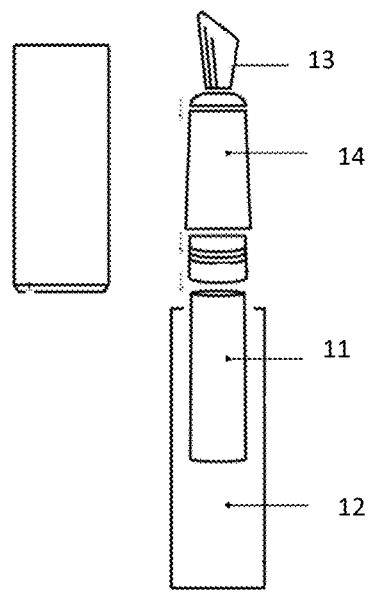
FIG. 7 shows a casing containing a refill.

Considering, for example, as shown in FIG. 7, the casing 12 to be used as a lipstick or gloss, the color contained in the refill 11, reaches the outer brush 13 of the casing through a removable washable support 14. In this way, the outer brush 13 never comes into contact with the ink inside the capsule, thus preserving the hygienic state of the ink inside the capsule itself. At the base of the support and internally, there is a sharp fixed part that is able to pierce the capsule at the time of the first insertion of the new capsule inside the base of the lip gloss. A new refill 11 can easily be inserted into the casing 12 once the previous refill has been used up.

Figure 6:
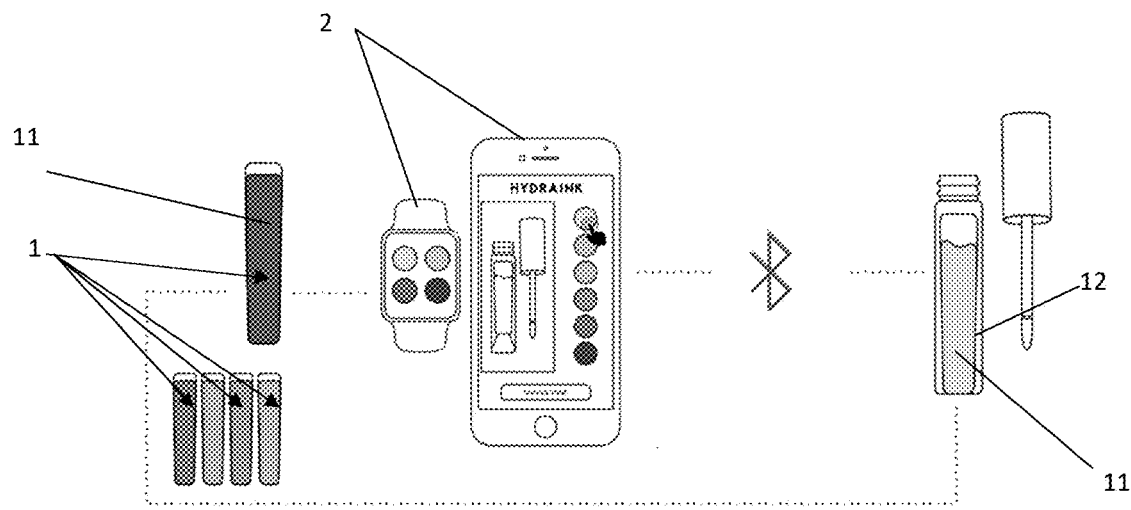
FIG. 6 shows a simplified diagram of the system according to a further embodiment of the present invention, which does not provide the wearable electronic device.
Figure 9:
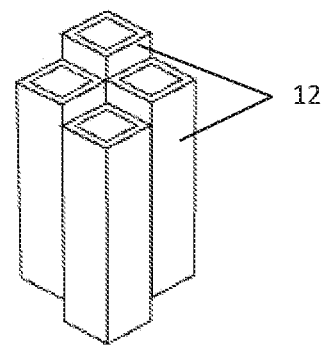
FIGS. 9A, 9B and 9C show examples of embodiments of combinations of refill holders.
Figure 9B:
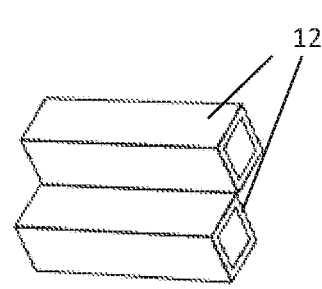
Figure 9C:
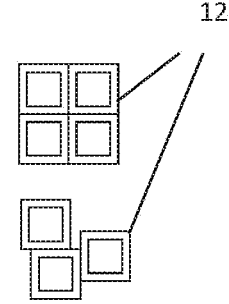

Advantageously, the innovative casing 12, as shown in FIG. 6, is highly technological and is able to contain and manage the capsules of dynamic make-up products; in this way the color change can also take place directly inside the casing 12 itself that communicates wirelessly directly with the computer application and has inside it the magnetic field emitter, the wireless antenna and the necessary electronic components. Moreover, each casing 12 is made in the form of a parallelepiped, with all the magnetic side surfaces, so as to create all combinations of shapes comprising several parallelepiped casings joined together by the magnetic force, as schematically and exemplifying shown in FIGS. 9A, 9B and 9C. In this way it will be possible to create compositions of casings 12 which can be adapted for all the available spaces.

Although at least one exemplary embodiment has been presented in the summary and in the detailed description, it must be understood that there exists a large number of variants falling within the scope of protection of the invention. Furthermore, it must be understood that the embodiment or the embodiments presented are only examples that do not intend to limit in any way the scope of protection of the invention or its application or configurations. Rather, the brief description and the detailed description provide the skilled man with a convenient guide for implementing at least one exemplary embodiment, as it is clear that numerous variations can be made in the function and assembly of the elements described therein, without departing from the scope of protection of the invention as established by the attached claims and their technical-legal equivalents.

What is claimed is:

1. A method for a variation of a color of a dynamic make-up product containing magneto-chromatic microspheres, comprising the following steps:
   applying the dynamic make-up product to a desired part of a human face or nails;
   selecting a color to be obtained for the applied dynamic make-up product using a computer mobile application loaded on a portable device,
   wherein the computer mobile application communicates wirelessly a polarity and intensity of a magnetic field, which is to be applied to the applied dynamic make-up product to obtain the selected color, to a wearable electronic device having within it a wireless communication system and a magnetic emitter;
   approaching the wearable electronic device to the applied make-up product wherein the magnetic emitter generates the magnetic field to cause the magneto-chromatic microspheres contained in the dynamic make-up product to change their orientation to display said selected color.

2. The method according to claim 1, wherein said portable device is selected from a smart phone or a smart watch.

* * * * *